United States Patent
Wei et al.

(10) Patent No.: US 6,473,636 B1
(45) Date of Patent: Oct. 29, 2002

(54) VARIABLE-LENGTH CORRELATION METHOD FOR MOTION CORRECTION IN SPECT MYOCARDIAL PERFUSION IMAGING

(75) Inventors: Guo-Qing Wei, Plainsboro, NJ (US); Jianzhong Qian, Princeton, NJ (US); Eric Q. Chen, Bartlett, FL (US); John C. Engdahl, Lake Forest, IL (US)

(73) Assignee: Siemens Corporate Research, Inc., Princeton, NJ (US)

(*) Notice: Subject to any disclaimer, the term of this patent is extended or adjusted under 35 U.S.C. 154(b) by 0 days.

(21) Appl. No.: 09/496,764

(22) Filed: Feb. 3, 2000

(51) Int. Cl.[7] .................................................. A61B 5/05
(52) U.S. Cl. .................. 600/436; 250/363.02; 382/128; 128/922
(58) Field of Search ................................. 600/436, 407, 600/425; 250/363.02; 382/128; 128/922

(56) References Cited

U.S. PATENT DOCUMENTS

| | | | | |
|---|---|---|---|---|
| 5,758,645 A | * | 6/1998 | Qian | 250/363.02 |
| 5,803,914 A | * | 9/1998 | Ryals et al. | 128/922 |
| 5,859,922 A | * | 1/1999 | Hoffmann | 382/128 |

* cited by examiner

Primary Examiner—Marvin M. Lateef
Assistant Examiner—Eleni Mantis Mercader
(74) Attorney, Agent, or Firm—Donald B. Paschburg (57) ABSTRACT

According to one embodiment of the invention, a variable length correlation method is provided for compensating for body motions and heart creep in a sequence of image frames obtained by single-photon emission computed tomograph (SPECT) myocardial perfusion imaging. Abrupt body motions, gradual body motions, and heart upward creep are detected and corrected in the sequence of image frames, based on varying correlation lengths. A linear transformation is used to compensate for appearance changes of the heart under different acquisition angles so as to achieve high accuracy of motion detection and correction. The detecting and correcting step is applied in the two-dimensional image domain. The method also includes the steps of detecting and excluding high intensity, non-heart regions in a particular image frame so that non-heart motions such as bowel gas, spleen, and liver motions are excluded from being involved in the motion detection and correction procedure.

24 Claims, 6 Drawing Sheets

(b) segmented blobs for position and shape analysis

VARIABLE-LENGTH CORRELATION METHOD FOR MOTION CORRECTION IN SPECT MYOCARDIAL PERFUSION IMAGING

BACKGROUND

1. Technical Field

The present invention is generally related to medical imaging and, in particular, to a variable-length method for correcting body motions and heart upward creep in Single-Photon Emission Computed Tomograph (SPECT) myocardial perfusion imaging in nuclear medicine.

2. Background

The single-photon emission computed tomograph (SPECT) myocardial perfusion imaging has been widely used in the diagnosis of coronary artery diseases. Since the whole image acquisition process usually takes more than 20 minutes, it is difficult for the patient to completely lie still during the acquisition. Also, heart upward creep occurs frequently during stress studies. Both heart upward creep and patient body motion during myocardial SPECT data acquisition may cause image artifacts (distortions of the appearance of the object of interest, such as the misalignment of the anterior and posterior walls of the left ventricle), resulting in potential false diagnosis. To reduce false positive diagnosis, both body motions and heart creep need to be post-corrected.

Prior art methods for correcting these motions are generally restricted to abrupt body motions. A brief description of some of these prior art methods will now be given.

The decomposition of body motion into axial (y) and trans-axial (x) components by projecting the images onto the x- and y-axes of the image plane is described by Eisner et al., in "Use of Cross-Correlation Function to Detect Patient Motion During SPECT Imaging", Journal of Nuclear Medicine, Vol.28, No.1, 1987, pp.97–101. Each motion component is estimated independently by cross-correlating the projected images of adjacent frames. However, as noted in the Eisner article, this procedure is unable to detect both gradual body motion and heart creep, since adjacent image frames for gradual motions and heart creep do not exhibit significant differences. Moreover, because of information loss in the projection of a 2D image into two 1D images, the method may either underestimate or overestimate the motions.

U.S. Pat. No. 5,758,645, entitled "Automatic Detection and Correction of Body Organ Motion and Particular Cardiac Motion in Nuclear Medicine Studies", issued on Jun. 2, 1998, assigned to the assignee herein, the disclosure of which is incorporated herein by reference, describes the estimation of body motions by minimizing the second order derivatives of the 1D projection images. However, this method does not explicitly address gradual body motions and heart creep.

The diverging square method, described by Geckle et. al., in "Correction for Patient and Organ Movement in SPECT: Application to Exercise Thallium-201 Cardiac Imaging", Journal of Nuclear Medicine, Vol.29, No. 4, 1998, pp.441–450, uses a growing square to track the heart. If the heart could be tracked accurately, virtually all kinds of motions could be dealt with. Unfortunately, for rest-injected and redistribution Thallium studies with high uptake regions such as the liver, the square may be wrongly trapped. Also, since hearts vary in size, the use of a fixed upper limit for growing the square may cause errors.

The two-dimensional fit method, described by Cooper et. al., in "Detection of Patient Motion During Tomographic Myocardial Perfusion Imaging", Journal of Nuclear Medicine, Vol.34, No.8, 1993, pp.1341–1348, puts a circular "Region Of Interest" (ROI) on the heart, and finds the body motion by correlating the ROI of the current image with the next image. This method was reported to be able to more accurately estimate motions than the decomposition-based 1D method. However, similar to the decomposition-based 1D method, gradual body motions and heart upward creep were not addressed.

In the prior art approaches, an ROI usually needs to be selected manually to cover the heart and to turn off effects of non-heart motions, such as bowel gas motions. This induces interactive work. Accordingly, it would be desirable and highly advantageous to have a fully automatic method for accomplishing the same. In particular, it would be desirable and highly advantageous to have an automatic method for correcting both body motion and heart upward creep in SPECT myocardial perfusion imaging.

SUMMARY OF THE INVENTION

The present Invention is directed to a method for motion correction in SPECT myocardial perfusion imaging. The method detects and corrects abrupt body motions, gradual body motions, and heart upward creep.

According to a first aspect of the invention, a variable length correlation method is provided for compensating for body motions and heart creep in a sequence of image frames obtained by single-photon emission computed tomograph (SPECT) myocardial perfusion imaging. The method includes the step of determining whether a bright spot corresponding to a non-heart motion exists in a particular image frame. The y-coordinate lower limit of the particular image frame is set as an offset from the position of the bright spot, when the bright spot exists. The y-coordinate lower limit of the particular image is set as an offset from the bottom of the particular image frame, when the bright spot does not exist. Abrupt body motions, gradual body motions, and heart upward creep are detected and corrected in the sequence of image frames, based on varying correlation lengths. The detecting and correcting step is applied in the two-dimensional image domain.

According to a second aspect of the invention, the determining step includes the step of determining consistency of sizes and positions of binarized image blobs using multiple thresholds.

According to a third aspect of the invention, the determining step includes the step of binarizing a given image frame by successively lowering a threshold value. Connected regions in the given image are identified. Pre-identified characteristics of each of the connected regions are determined. A given connected region is identified as a bright spot corresponding to a non-heart motion, when the pre-identified characteristics of the given connected region correspond to predetermined criteria.

According to a fourth aspect of the invention, the pre-identified characteristics include at least some of the area, the center of gravity, the x-size, and the y-size.

According to a fifth aspect of the invention, the predetermined criteria include at least some of the x and y size-ratio being within a first pre-specified limit, the area being within a second pre-specified limit, and continuous changes across the multiple thresholds.

According to a sixth aspect of the invention, the detecting and correcting step includes the step of comparing a given image frame to earlier image frames of varying distances from the given image frame.

According to a seventh aspect of the invention, the detecting and correcting step includes the step of comparing a given image frame to at least one earlier image frame having a predefined distance from the given image frame, for each of abrupt body motions, gradual body motions, and heart upward creep, respectively.

According to an eighth aspect of the invention, abrupt body motions, gradual body motions, and heart upward creep are each determined and corrected during a separate pass of the method. Each of the separate passes include the step of comparing a given image frame to at least one earlier image frame having a predefined distance from the given image frame.

According to a ninth aspect of the invention, a first pass detects abrupt body motions, a second pass detects gradual body motions, and a third pass detects heart upward creep.

According to a tenth aspect of the invention, the detecting and correcting step includes the step of applying a linear transformation to at least some of the image frames to compensate for the x-directional appearance changes caused by viewing angle differences.

According to an eleventh aspect of the invention, the applying step includes the step of applying the linear transformation to one of every two of the image frames.

These and other aspects, features and advantages of the present invention will become apparent from the following detailed description of preferred embodiments, which is to be read in connection with the accompanying drawings.

DETAILED DESCRIPTION OF PREFERRED EMBODIMENTS

The present invention is directed to a method for motion correction in SPECT myocardial perfulsion imaging. The method is based on variable length correlation in the original 2D image domain. By varying the correlation length, motions are detected and corrected in multiple passes. The variable length 2D correlation compares the current frame with frames of variable distances and, thus, provides information of body motion and heart creep in different scales. According to an illustrative embodiment of the method of the invention, a first pass detects and corrects abrupt body motions, a second pass detects and corrects gradual body motions, and a third pass detects and corrects heart upward creep.

As part of the variable length correlation method of the invention, a linear transformation is applied to one of the 2D images in the correlation measure. This linear transformation is intended to compensate for appearance changes of the heart under different image acquisition angles.

To exclude non-heart motions such as, for example, bowel gas, spleen, and liver motions, the invention utilizes the fact that such motions frequently appear as a very bright, round spot moving in the lower part of the images. Thus, by successively lowering a threshold and analyzing the size and position contiguities of binarized image blobs, the potential positions of such non-heart motions can be localized. A lower y-limit on the image coordinates can thus be selected accordingly.

Figure 1A:
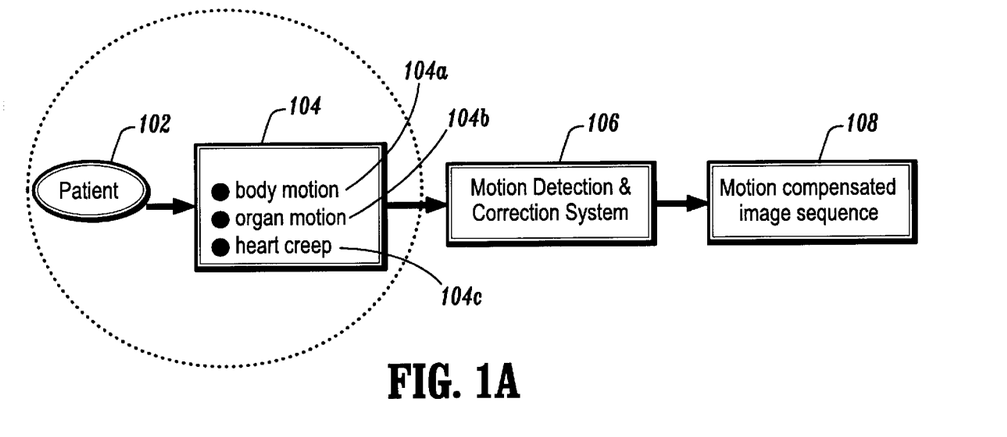
FIG. 1A is a diagram illustrating the input and output of a method for motion correction in SPECT Myocardial Perfusion Imaging according to an illustrative embodiment of the present invention.
Figure 1B:
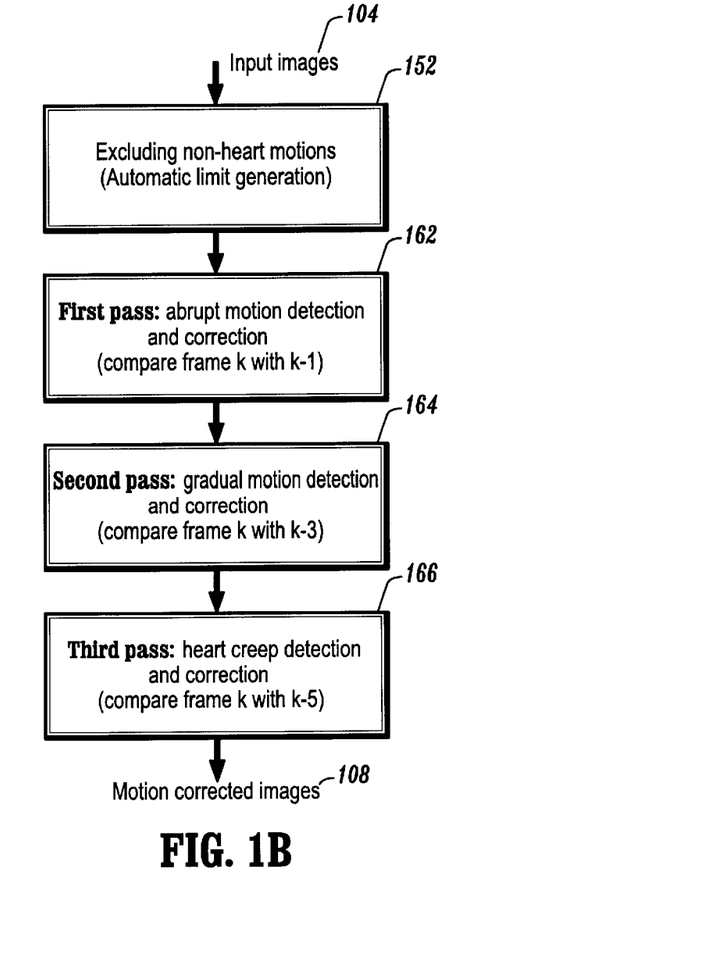
FIG. 1B is a flow diagram illustrating the method for motion correction in SPECT Myocardial Perfusion Imaging according to the illustrative embodiment of FIG. 1A.

FIG. 1A is a diagram illustrating the input and output of a method for motion correction in SPECT Myocardial Perfusion Imaging according to an illustrative embodiment of the present invention. FIG. 1B is a flow diagram illustrating the method for motion correction in SPECT Myocardial Perfusion Imaging according to the illustrative embodiment of FIG. 1A. It is to be noted that the terms "corrected" and "compensated" are used interchangeably herein.

From a patient 102, images 104 corresponding to body motion 104a, organ motion 104b, and heart creep 104c are obtained. The images 104 are applied to the method 106 of the present invention (e.g., the method of FIG. 1B described below), and a motion compensated image sequence 108 is output therefrom.

As shown in FIG. 1B, non-heart motions are excluded (step 152). In the first pass of the method 106, abrupt motion is detected and corrected (step 162). In the second pass, gradual motion is detected and corrected (step 164). In the third pass, heart creep is detected and corrected (step 166). The motion compensated image sequence 108 is then output.

Figure 2A:
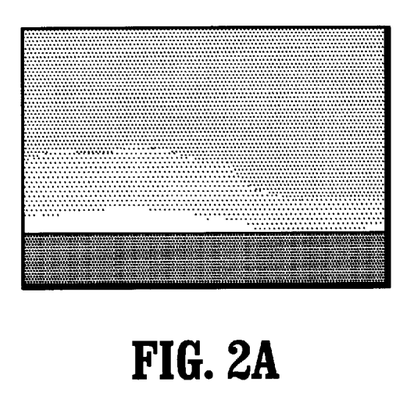
FIG. 2 is a diagram illustrating the detection and correction of different motions during each pass of the method of the present invention according to an illustrative embodiment thereof.
Figure 2B:
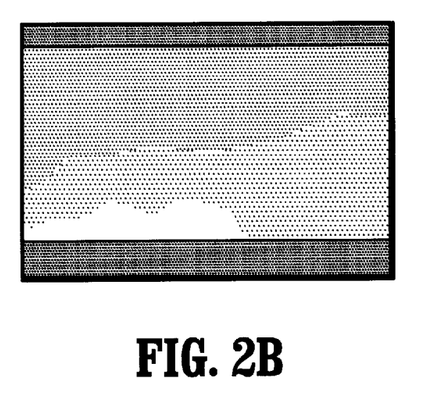

FIG. 2. is a diagram illustrating the detection and correction of different motions during each pass of the method of the present invention, according to an illustrative embodiment thereof In particular, FIG. 2(a) is a visualization of a SPECT image sequence of 64 frames in terms of image projection. Each image in the original sequence is summed along the x-axis to produce a column image. The column images are stacked together to become the image shown in FIG. 2(a). FIG. 2(b) is the same image sequence with simulated body motions and heart creep added. The image sequence with added motions is the input to the method described here to illustrate the effect of motion correction.

One of the central ideas of the present invention is to detect motions from the viewpoint of motion scales. With different values of the scale parameter or the correlation length Δk, different kinds of motions are detected in the way that frame k is compared with frame k−Δk. For example, abrupt motions are detected with a scale of Δk=1, while gradual motions are detected with a scale of Δk=3. Heart upward creep is more subtle and, thus, needs a still larger scale, for example, Δk=5. The above scales are provided for illustrative purposes and, thus, other scales may be used. Given the teachings of the present invention provided herein, one of ordinary skill in the related art will be able to contemplate these and similar implementations of the elements of the invention.

Figure 3:
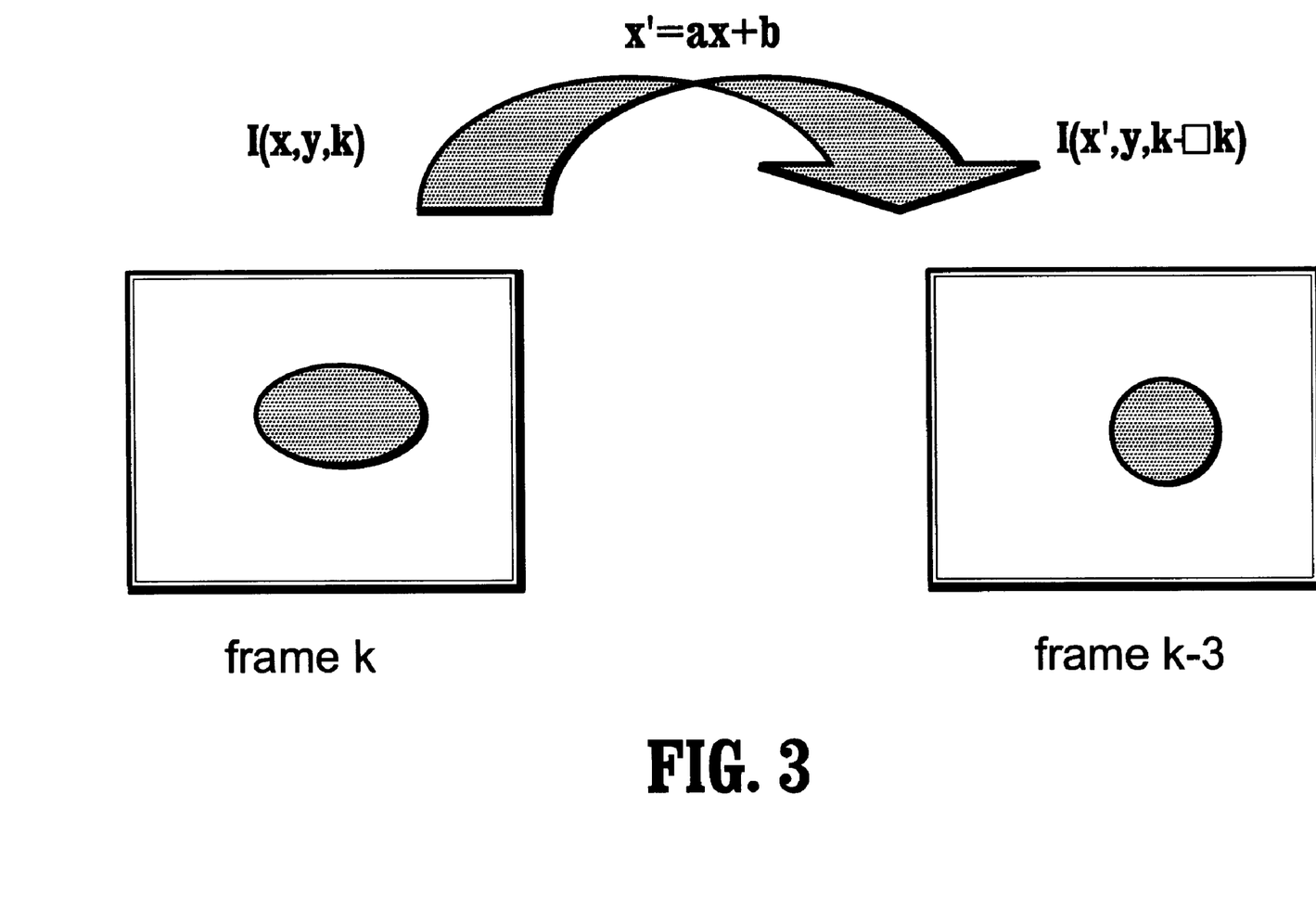
FIG. 3 is a diagram illustrating normalization of the appearance of the heart through a linear transformation according to an illustrative embodiment of the present invention.

In SPECT imaging, frame numbers correspond to indices of the image acquisition angle. The larger the correlation length Δk, the bigger the difference between the acquisition angles of the two correlation frames. Thus, a large value may cause substantial appearance changes of the heart in the two images k and k−Δk, e.g., the heart may become elongated or shortened in the x-direction. It is to be noted that in the y-direction, there is no such elongating or shortening effect, since the movement of the camera is perpendicular to the body axis. The above appearance change in the x-direction needs to be compensated when performing motion estimation between frame k and k−Δk. Since the SPECT imaging is a parallel projection, the x-directional shape changes can be approximated by a linear transformation. FIG. 3 is a diagram illustrating the transformation of an elongated heart back to its circular shape through the use of a linear transformation according to an illustrative embodiment of the present invention. Here x'=ax+b is the transformation used, and (a,b) are the transformation parameters. Preferably, but not necessarily, the linear transformation is applied to one of every two image frames.

Since the linear transformation used in the x-direction is unknown, the transformation parameters have to be estimated at the same time as motion parameters. The correlation between frame k and k−Δk is realized by image difference, as illustrated by the following minimization:

$$\min_{a,b,v} E(a, b, v) = \min_{a,b,v} \sum_x \sum_y (I(ax+b, y+v, k) - I(x, y, k-\Delta k))^2 \quad (1)$$

where $I(x,y,k)$ represents the intensity function of the k-th frame, (a,b) are the linear transformation parameters in the x-direction, and v is the y-directional motion between frame k and k−Δk. For Δk=1, which is used to detect abrupt motions in the above example, the x-directional appearance change can be ignored. Thus, by letting a=1, the physical meaning of b becomes the x-directional body motion between frame k and k−1. Therefore, with Δk 1, both x and y directional body motions are detected and corrected. After that, larger correlation lengths are used to detect and correct gradual body motions and heart upward creep. It is to be noted that gradual body motions in the transaxial directions are less likely to happen and, thus, are not considered here.

To minimize Eq. (1), a gradient descent search with bilinear image interpolation is used. The procedure iteratively updates the parameters a, b and v until convergence is reached. The update rule for each parameter is $$\Delta a = -\frac{\partial E}{\partial a} = -\sum_x \sum_y [I(a^n x + b^n, y + v^n, k) - I(x, y, k - \Delta k)]$$

$$I_x(a^n x + b^n, y + v^n, k)x$$

-continued $$\Delta b = -\frac{\partial E}{\partial b} = -\sum_x \sum_y [I(a^n x + b^n, y + v^n, k) - I(x, y, k - \Delta k)]$$

$$I_x(a^n x + b^n, y + v^n, k)x$$

$$\Delta v = -\frac{\partial E}{\partial v} = -\sum_x \sum_y [I(a^n x + b^n, y + v^n, k) - I(x, y, k - \Delta k)]$$

$$I_y(a^n x + b^n, y + v^n, k)$$

where a", b" and v" are the values at the n-th iteration.

It is to be appreciated that the present invention is not limited to the preceding function minimization procedure and, thus, other function minimization procedures may be employed in accordance with the present invention while maintaining the spirit and scope thereof. According to a preferred embodiment of the present invention, the linear transformation and gradient descent function minimization are applied at each pass of the variable correlation method.

Figure 2C:
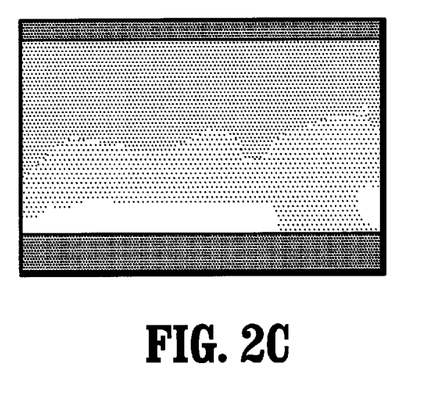
Figure 2D:
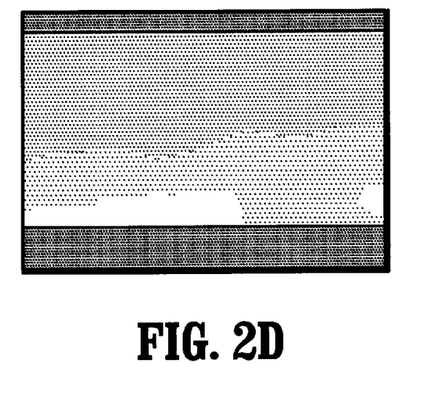
Figure 2E:
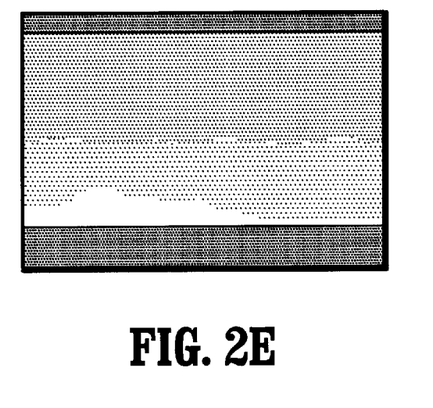

FIG. 2(c), (d), (e) illustrate the corrected image sequences after the 1st pass, the 2nd pass, and the 3rd pass, respectively.

For technetium Sestamibi (MIBI) studies, typically a very bright, round spot underneath the heart moves up and down independent of the body motion. This non-heart motion frequently corresponds to bowel gas motions. If non-heart motions such as bowel gas motions interfere with the body motion estimation, the accuracy of the body motion estimation will degrade. To avoid this problem in the prior art, a lower limit in the y-axis of the image plane was set manually. The present invention is able to detect this region automatically and, thus, find an appropriate lower limit in an autonomous way.

Figure 4A:
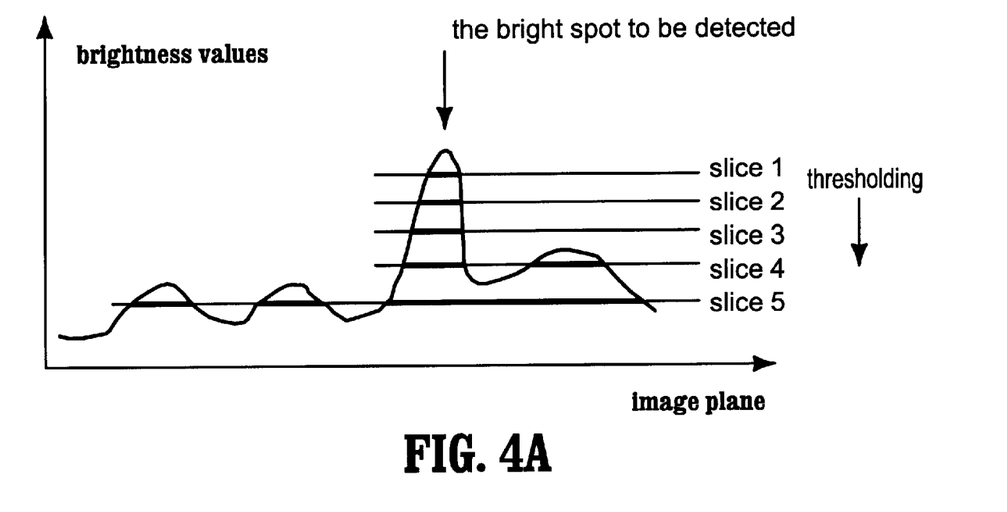
FIG. 4A is a diagram illustrating multiple thresholding segmentation in the determination of a bright spot corresponding to a non-heart motion according to an illustrative embodiment of the present invention.
Figure 4B:
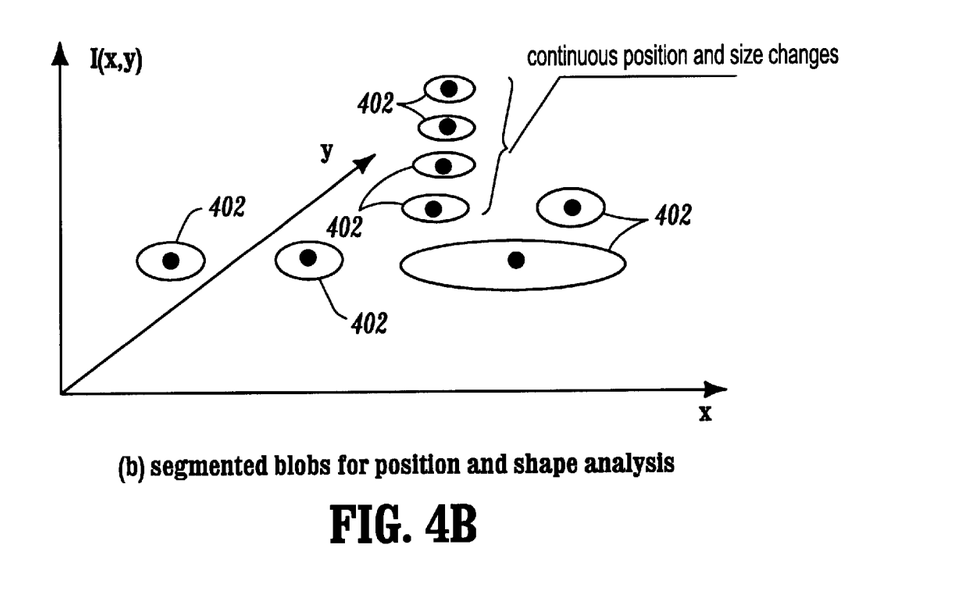
FIG. 4B is a diagram illustrating segmented blobs for position and shape analysis in the determination of a bright spot corresponding to a non-heart motion according to an illustrative embodiment of the present invention.

FIG. 4A is a diagram illustrating multiple thresholding segmentation in the determination of a bright spot corresponding to a non-heart motion according to an illustrative embodiment of the present invention. FIG. 4B is a diagram illustrating segmented blobs for position and shape analysis in the determination of a bright spot corresponding to a non-heart motion according to an illustrative embodiment of the present invention. The basic idea is to successively lower a threshold value (y-axis in FIG. 4A) to binarize the image (only the first frame is needed for this analysis). The binarized images are then analyzed to find connected regions (blobs). The area, center of gravity, the x-size, and y-size of each blob 402 are computed. The regions with continuous position changes across threshold levels, whose x and y size-ratio does not exceed 3, and whose area does not exceed 30 pixels, are selected as the bowel gas positions. An offset from this position is used as the lower y-coordinate limit for motion estimation.

Figure 5:
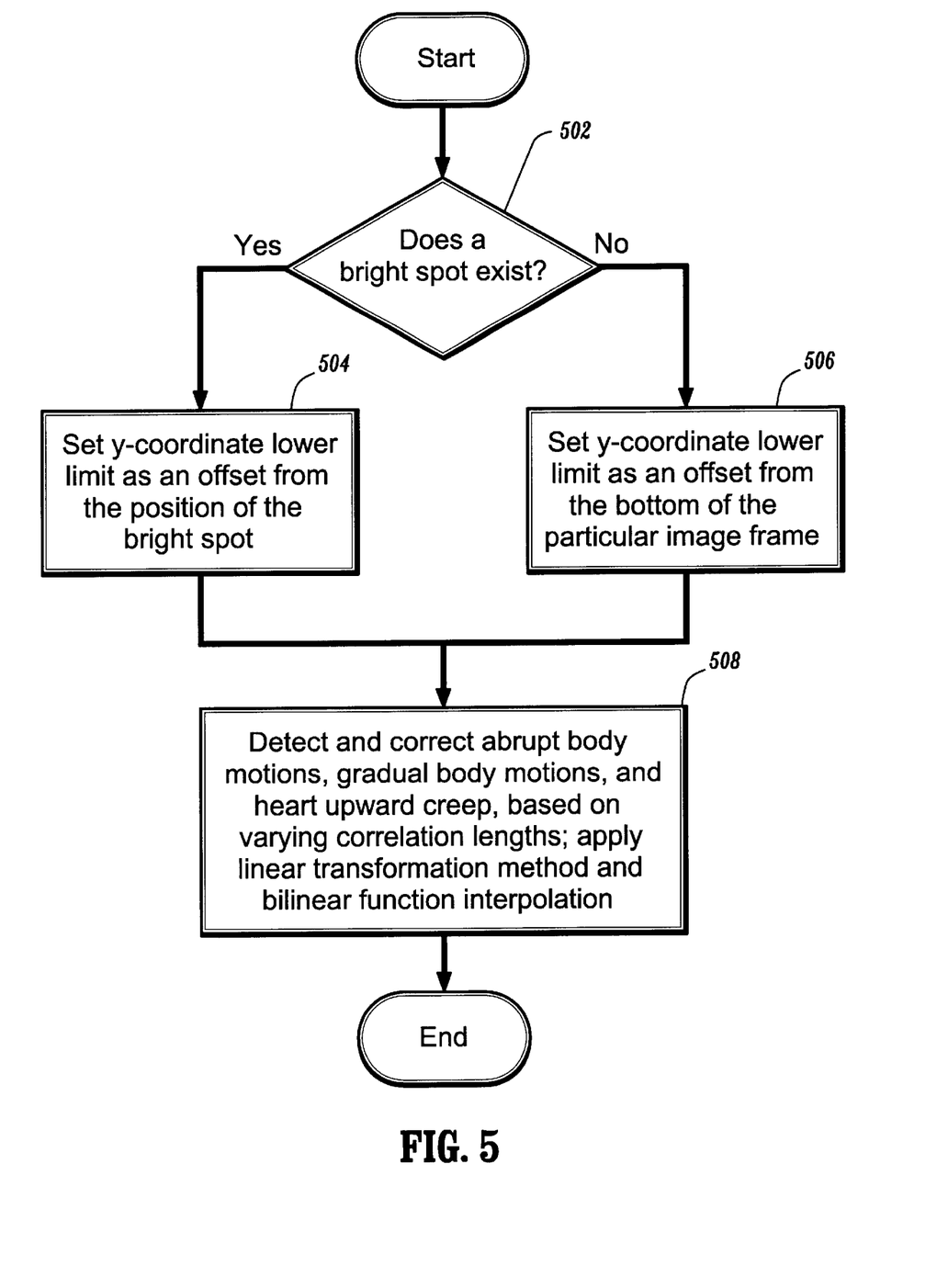
FIG. 5 is a flow diagram illustrating a variable length correlation method for compensating for body motions and heart creep in a sequence of image frames obtained by single-photon emission computed tomograph (SPECT) myocardial perfusion imaging according to an illustrative embodiment of the present invention.

FIG. 5 is a flow diagram illustrating a variable length correlation method for compensating for body motions and heart creep in a sequence of image frames obtained by single-photon emission computed tomograph (SPECT) myocardial perfusion imaging according to an illustrative embodiment of the present invention. It is determined whether a bright spot corresponding to a non-heart motion exists in a particular image frame (step 502). The y-coordinate lower limit of the particular image frame is set as an offset from the position of the bright spot, when the bright spot exists (step 504). The y-coordinate lower limit of the particular image frame is set as an offset from the bottom of the particular image frame, when the bright spot does not exist (step 506). Abrupt body motions, gradual body motions, and heart upward creep in the sequence of image frames are detected and corrected, based on varying correlation lengths (step 508). Step 508 is applied in the two-dimensional image domain. Step 508 is shown in further detail in FIG. 1B above, according to an illustrative embodiment of the present invention. Step 508 also contains the application of a linear transformation to compensate for the x-directional appearance changes caused by viewing angle differences. A gradient descent method (with bilinear image interpolation) is used to minimize the correlation function to achieve sub-pixel accuracy of motion estimation in step 508.

Figure 6:
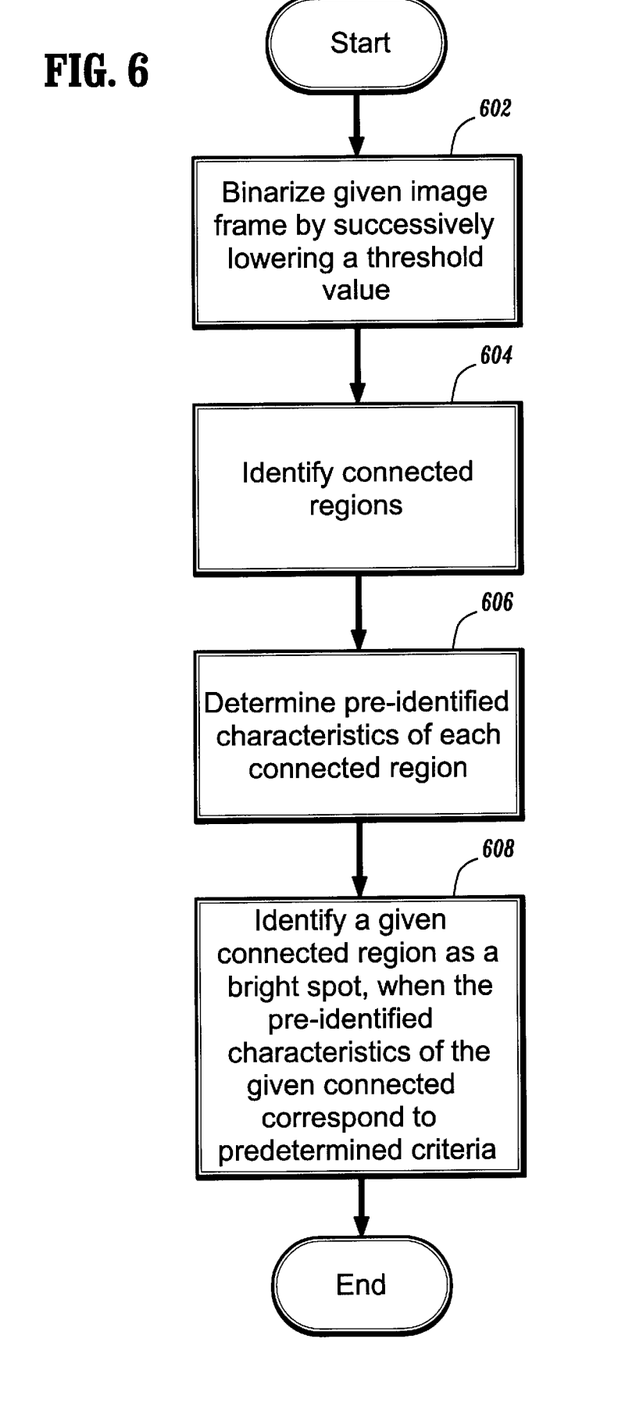
FIG. 6 is a flow diagram illustrating step 502 of FIG. 5 according to an illustrative embodiment of the present invention.

FIG. 6 is a flow diagram illustrating step 502 of FIG. 5 according to an illustrative embodiment of the present invention. A given image frame is binarized by successively lowering a threshold value (step 602). Connected regions in the given image are identified (step 604). Pre-identified characteristics (e.g., area, center of gravity, x-size, and y-size) of each of the connected regions are determined (step 606). A given connected region is identified as a bright spot corresponding to a non-heart motion, when the pre-identified characteristics of the given connected region corresponds to predetermined criteria (e.g., having continuous changes across the multiple thresholds, an x and y size-ratio within a first pre-specified limit, and an area within a second pre-specified limit) (step 608).

Although the illustrative embodiments have been described herein with reference to the accompanying drawings, it is to be understood that the present system and method is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A variable length correlation method for compensating for body motions and heart creep in a sequence of image frames obtained by single-photon emission computed tomograph (SPECT) myocardial perfusion imaging, comprising the steps of:

determining whether a bright spot corresponding to a non-heart motion exists in a particular image frame;

automatically setting a y-coordinate lower limit of the particular image frame as an offset from a position of the bright spot, when the bright spot exists;

automatically setting the y-coordinate lower limit of the particular image as an offset from a bottom of the particular image frame, when the bright spot does not exist; and detecting and correcting abrupt body motions, gradual body motions, and heart upward creep in the sequence of image frames, based on varying correlation lengths, wherein said said detecting and correcting step is applied in the two-dimensional image domain.

2. The method according to claim 1, wherein said determining step comprises the step of determining consistency of sizes and positions of binarized image blobs using multiple thresholds.

3. The method according to claim 1, wherein said determining step comprises the steps of:

binarizing a given image frame by successively lowering a threshold value;

identifying connected regions in the given image;

determining pre-identified characteristics of each of the connected regions; and identifying a given connected region as the bright spot, when the pre-identified characteristics of the given connected region corresponds to predetermined criteria.

4. The method according to claim 3, wherein the pre-identified characteristics comprise at least some of an area, a center of gravity, an x-size, and a y-size.

5. The method according to claim 3, wherein the predetermined criteria comprise at least some of an x and y size-ratio being within a first pre-specified limit, an area being within a second pre-specified limit, and continuous changes across the multiple thresholds.

6. The method according to claim 1, wherein said detecting and correcting step comprises the step of comparing a given image frame to earlier image frames of varying distances from the given image frame.

7. The method according to claim 1, wherein said detecting and correcting step comprises the step of comparing a given image frame to at least one earlier image frame having a predefined distance from the given image frame, for each of the abrupt body motions, the gradual body motions, and the heart upward creep, respectively.

8. The method according to claim 7, wherein said detecting and correcting step comprises the step of applying a gradient descent method and a bilinear function interpolation to minimize a correlation function corresponding to the given image frame and the at least one image frame, so as to achieve sub-pixel accuracy of motion estimation.

9. The method according to claim 1, wherein the abrupt body motions, the gradual body motions, and the heart upward creep are each determined and corrected during a separate pass of said method, wherein each of the separate passes comprises the step of comparing a given image frame to at least one earlier image frame having a predefined distance from the given image frame.

10. The method according to claim 1, wherein a first pass detects the abrupt body motions, a second pass detects the gradual body motions, and a third pass detects the heart upward creep.

11. The method according to claim 1, wherein said detecting and correcting step comprises the step of applying a linear transformation to at least some of the image frames to compensate for the x-directional appearance changes caused by viewing angle differences.

12. The method according to claim 11, wherein said applying step comprises the step of applying the linear transformation to one of every two image frames.

13. A variable length correlation method for compensating for body motions and heart creep in a sequence of image frames obtained by single-photon emission computed tomograph (SPECT) myocardial perfusion imaging, comprising the steps of:

automatically setting a y-coordinate lower limit of a particular image frame as an offset from a position of a bright spot corresponding to a non-heart motion, when the bright spot exists in the particular image frame; and detecting and correcting abrupt body motions, gradual body motions, and heart upward creep in the sequence of image frames, wherein said detecting and correcting step is applied in the two-dimensional image domain, and includes the step of comparing a given image frame to at least one earlier image frame having a predefined distance from the given image frame, for each of the abrupt body motions, the gradual body motions, and the heart upward creep, respectively.

14. A program storage device readable by machine, tangibly embodying a program of instructions executable by the machine to perform method steps for compensating for body motions and heart creep in a sequence of image frames obtained by single-photon emission computed tomograph (SPECT) myocardial perfusion imaging, the method based on variable length correlation, and comprising the steps of:

determining whether a bright spot corresponding to a non-heart motion exists in a particular image frame;

automatically setting a y-coordinate lower limit of the particular image frame as an offset from a position of the bright spot, when the bright spot exists;

automatically setting the y-coordinate lower limit of the particular image as an offset from a bottom of the particular image frame, when the bright spot does not exist; and detecting and correcting abrupt body motions, gradual body motions, and heart upward creep in the sequence of image frames, based on varying correlation lengths, wherein said detecting and correcting step is applied in the two-dimensional image domain.

15. The program storage device according to claim 14, wherein said determining step comprises the step of determining consistency of sizes and positions of binarized image blobs using multiple thresholds.

16. The program storage device according to claim 14, wherein said determining step comprises the steps of:

binarizing a given image frame by successively lowering a threshold value;

identifying connected regions in the given image;

determining pre-identified characteristics of each of the connected regions; and identifying a given connected region as the bright spot, when the pre-identified characteristics of the given connected region corresponds to predetermined criteria.

17. The program storage device according to claim 16, wherein the pre-identified characteristics comprise at least some of an area, a center of gravity, an x-size, and a y-size.

18. The program storage device according to claim 16, wherein the predetermined criteria comprise at least some of an x and y size-ratio being within a first pre-specified limit, an area being within a second pre-specified limit, and continuous changes across the multiple thresholds.

19. The program storage device according to claim 14, wherein said detecting and correcting step comprises the step of comparing a given image frame to earlier image frames of varying distances from the given image frame.

20. The program storage device according to claim 14, wherein said detecting and correcting step comprises the step of comparing a given image frame to at least one earlier image frame having a predefined distance from the given image frame, for each of the abrupt body motions, the gradual body motions, and the heart upward creep, respectively.

21. The program storage device according to claim 20, wherein said detecting and correcting step comprises the step of applying a gradient descent method and a bilinear function interpolation to minimize a correlation function corresponding to the given image frame and the at least one earlier image frame, so as to achieve sub-pixel accuracy of motion estimation.

22. The program storage device according to claim 14, wherein the abrupt body motions, the gradual body motions, and the heart upward creep are each determined and corrected during a separate pass of said method, wherein each of the separate passes comprises the step of comparing a given image frame to at least one earlier image frame having a predefined distance from the given image frame.

23. The program storage device according to claim 14, wherein a first pass detects the abrupt body motions, a second pass detects the gradual body motions, and a third pass detects the heart upward creep.

24. The program storage device according to claim 14, wherein said detecting and correcting step comprises the step of applying a linear transformation to at least some of the image frames to compensate for the x-directional appearance changes caused by viewing angle differences.

* * * * *